(12) United States Patent
Gittleman et al.

(10) Patent No.: US 6,417,007 B1
(45) Date of Patent: Jul. 9, 2002

(54) ROBOTIC HARVESTING OF SOLIDS FROM FLUIDS

(75) Inventors: Mark M. Gittleman, Seabrook; Rick C. Hunter, Friendswood; Norman L. Smith, Seabrook; Alistair P. Johnston, Houston, all of TX (US)

(73) Assignee: Oceaneering International Inc., Houston, TX (US)

( * ) Notice: Subject to any disclaimer, the term of this patent is extended or adjusted under 35 U.S.C. 154(b) by 0 days.

(21) Appl. No.: 09/441,850

(22) Filed: Nov. 17, 1999

Related U.S. Application Data
(60) Provisional application No. 60/108,741, filed on Nov. 17, 1998, and provisional application No. 60/114,071, filed on Dec. 28, 1998.

(51) Int. Cl.[7] .............................. G01N 1/04; B01L 3/02
(52) U.S. Cl. ...................... 436/180; 117/35; 117/206; 422/100; 422/929
(58) Field of Search .................... 422/99, 100, 101, 422/922, 929; 117/11, 30, 35, 200, 206, 219; 436/180

(56) References Cited

U.S. PATENT DOCUMENTS
4,919,899 A * 4/1990 Herrmann et al.
5,078,975 A * 1/1992 Rhodes et al.
5,221,410 A * 6/1993 Kushner et al.

OTHER PUBLICATIONS
"Practical Protein Crystallography", Duncan E. McRee, Academic Press, Inc. pp 21–29, Undated.

* cited by examiner

Primary Examiner—Joseph W. Drodge
(74) Attorney, Agent, or Firm—Kurt S. Myers

(57) ABSTRACT

The present invention is directed to the method and apparatus for the robotic harvesting of solids from liquids as exemplified by harvesting protein crystals. Further, the present invention is directed to a fluid/solid management system in a chamber that automates the task of solid harvesting. The fluid/solid management system includes two supporting structures for at least one pipette on one structure and a second pipette on the other structure, the two pipettes in tip-to-tip alignment. The pipettes each having a drop of liquid at the end thereof are moved apart to form a liquid bridge in which the solid crystal is isolated. A robotic arm has a device on the end thereof for the harvesting of the solid at the working point between the tips of the pipettes. The system has a flash freezing system in the chamber for the safe storage of the harvested solid.

12 Claims, 5 Drawing Sheets

ROBOTIC HARVESTING OF SOLIDS FROM FLUIDS

RELATED APPLICATIONS

This application is based on provisional applications Ser. Nos. 60/108,741, entitled "Automated Crystal Preparation, Examination, & Storage Facility", filed Nov. 17, 1998 and 60/114,071, entitled "Crystal-Harvesting Capillary Mounting Device", filed Dec. 28, 1998, both of which are incorporated herein in their entirety by reference.

FIELD OF THE INVENTION

The present inventions are directed to robotic solid harvesting methods and systems. The manipulation harvesting science embodied in the methods and devices of the present inventions are exemplified in protein crystal harvesting.

BACKGROUND OF THE INVENTION

The processes for producing protein crystals in the characterization of the proteins is a well developed science. The present processes are all very labor intensive and tedious to carry out. There is considerable art involved by the persons capturing the crystals produced and carrying out the tasks of identifying a crystal to harvest. The proteins are crystalized in a mother liquor and then manually removed from the mother liquor. The harvested crystal is then characterized by x-ray diffraction.

A full disclosure of the present methods used to prepare and isolate protein crystals are set forth in a book written by Ducan E. McRee, "Practical Protein Crystallography", Acedemic Press Inc., San Diego, Calif., 1993. What is made clear is that the present methods employed are done by hand on the bench with much skill. The art or skill necessary is due to the fragile nature of the protein crystals; first, in crystallizing the protein; second, in removing the crystal from the mother liquor or liquid; and then, in handling the crystal for the crystallography techniques carried out on the protein to fully characterize the protein.

It is the object of the present inventions to utilize robotic technologies to enable the harvesting and storing of solids from liquids. Robotic techniques allow the harvesting of solids to be done quicker and more easily by those persons presently carrying out such processes. The robotic techniques of the present invention solves the three dimensional problems of the havesting or capturing of the solids and resolves the harvesting to a one dimensional solution. The present invention is illustrated by the harvesting of solid protein crystals from mother liquors. The process permits the inspection of the crystal to be certain that a suitable crystal is harvested for the steps of flash freezing and x-ray diffraction. The present invention also addresses the harvesting of a crystal and the immediate flash freezing of the crystal to make the crystal more robust to the x-ray diffraction crystallography techniques that are carried out on the crystal.

SUMMARY OF THE INVENTIONS

The present invention is directed to the method and apparatus for the robotic harvesting of solids, especially small solids. Further, the present invention is directed to a fluid/solid management system that automates the task of solid harvesting. Still further, the present invention is directed to devices to harvest and store the solid as illustrated by protein crystals.

BRIEF DESCRIPTION OF THE EMBODIMENTS OF THE PRESENT INVENTIONS

The present invention is directed to a robotic solid harvesting system. The system is illustrated by the use of this robotic technology to perform the usual crystallography preparation techniques on solid crystals in an isolation chamber. The system is designed so that it may be used independently or with further systems that include (i) an x-ray diffraction system and (ii) a command, control and data management system.

The robotic harvesting system of the present invention consists of a suite of equipment that will enable remote and manual preparation of solids in a liquid and solid harvesting and mounting Optionally, the system also includes flash freezing, and frozen storage of the solid. The solid harvesting and mounting functions, the flash freezing and storage are done in an environmentally controlled glove box or enclosure.

Figure 1:
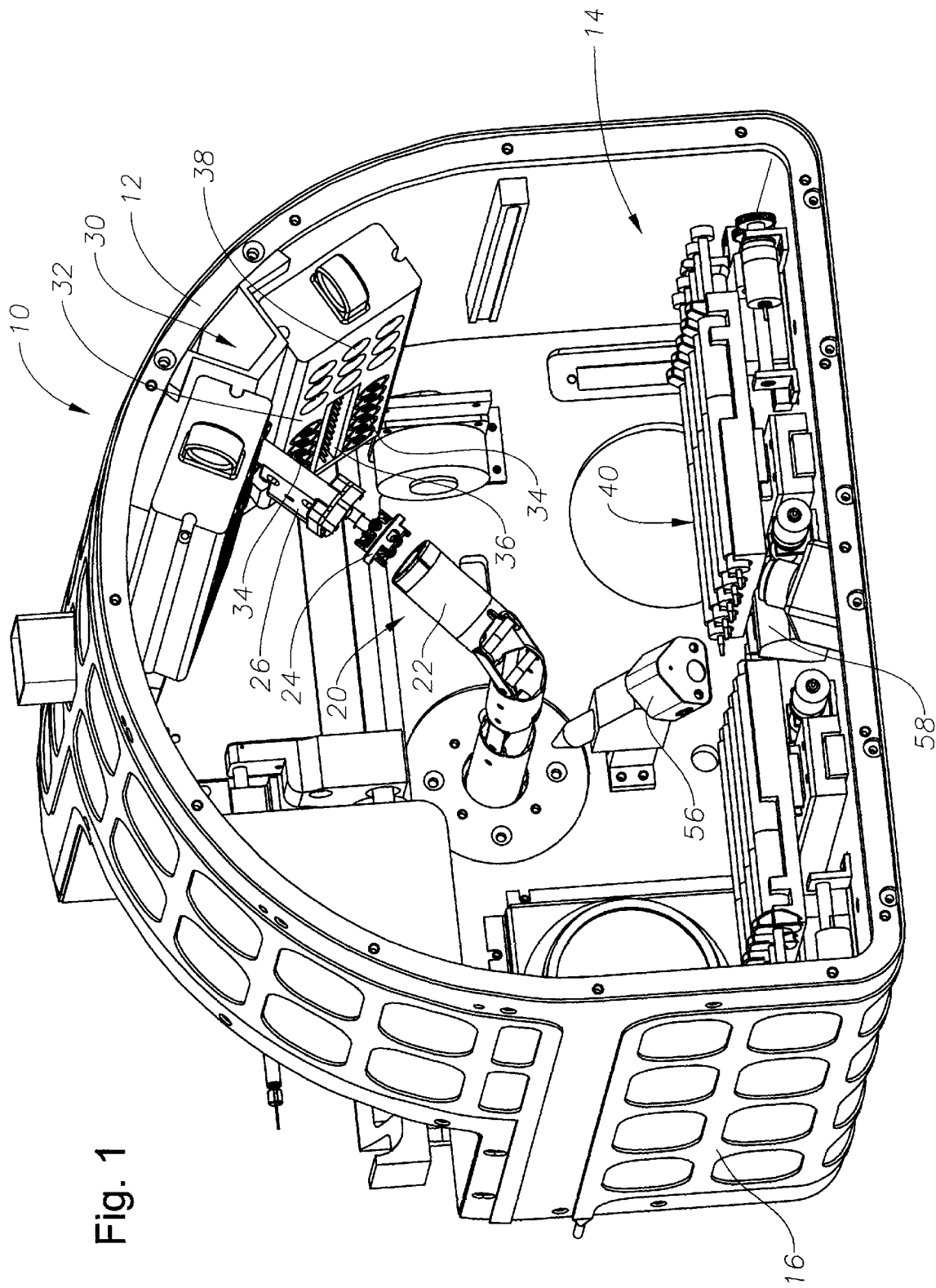
FIG. 1 is an isometric view of a solid harvesting system of the present invention including solid storage cells, a fluid/solid management system, and a flash freezing and storage system all included in a chamber.

Refering to FIG. 1, system 10 is a suite of equipment for the harvesting of protein crystals. A structured frame assembly 12 houses the system 10 and provides a working chamber 14. The front panel of the assembly 12 is removed and the gloved openings are not shown. A water jacket 16 is included in the structured frame of assembly 12 to control the desired internal temperature of the internal crystal working chamber 14. The major components of system 10 are shown in FIG. 1; namely, a robotic arm 20, a tool cartridge container 30, a fluid/solid management system 40 and a flash freezer 70.

Figure 2:
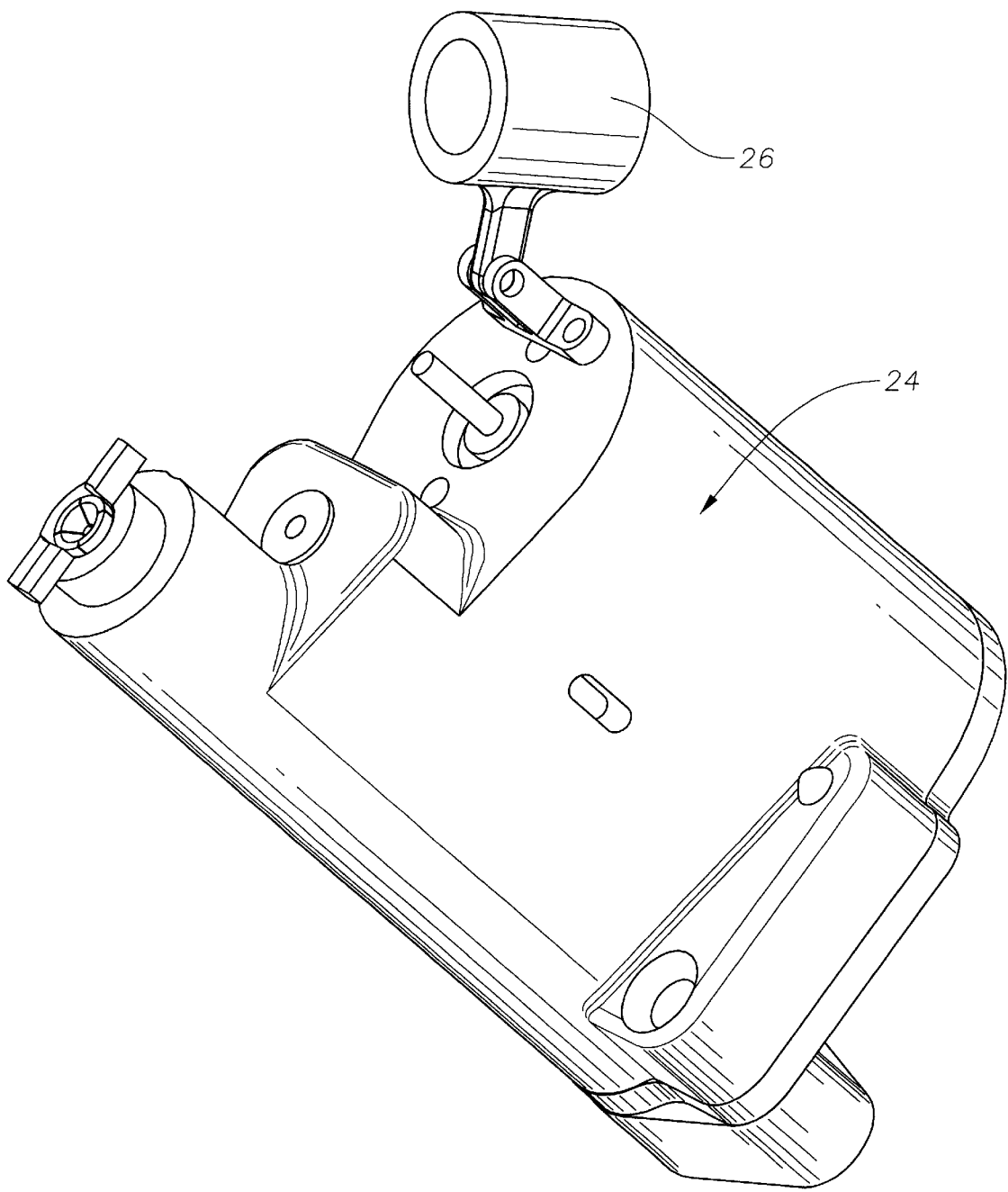
FIG. 2 is an isometric view of an end effector that serves as an interface between the micromanipulator and the solid harvesting chamber.

The robotic arm 20 performs the automated protein crystal harvesting tasks. The arm 20 has two parts, a manipulator 22 and an end effector 24. The degrees of freedom of the manipulator 22 enable it to perform actuation of linear and rotary motion. A preferred micromanipulator 22 is a Oceaneering OM3198 micromanipulator having the following degrees of freedom and joint ranges: shoulder roll—120°; shoulder pitch—360°; elbow pitch—360°; wrist roll—540°; wrist pitch—180°; and wrist yaw—180°. The end effector 24 serves as an interface between the micromanipulator 22 and the operations that take place in the chamber 14, as will be described hereinafter. The micromanipulator 22 also serves as mobile platform for the attached fiberscope camera 26 that serves as the prime visual inspection tool. The end effector is shown in more detail in FIG. 2.

A tool cartridge container 30 is positioned near the top and on one side of the chamber 14. The container 30 is attached to the assembly 12. Container 30 may hold two tool cartridges 32, only one being shown. Each cartridge 32 holds two high density protein crystal growth blocks 34, each block containing a plurality of cells that contain a high density of protein crystals in a mother liquor to be harvested. In addition, cartridges 32 hold at least twelve hairloop tools 36 and nine pipette tools 38. Blocks 34 and tools 36 and 38 are secured to the cartridge 32 until access and retrival is made by the end effector 24 attached to the micromanipulator 22 to carry out the desired operation.

Figure 3:
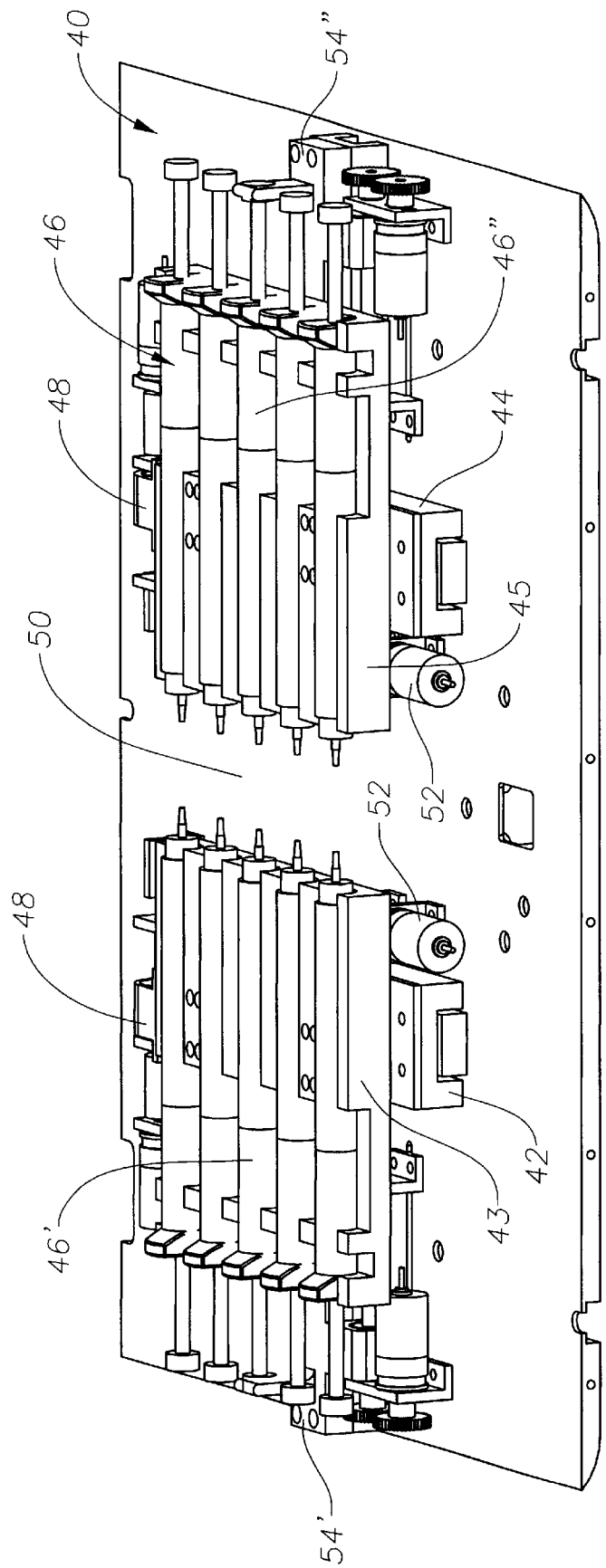
FIG. 3 is an isometric view of the fluid/solid management system on the floor of the chamber.

A fluid/solid management system 40 is located on the floor of the assembly 12. The function of the fluid/solid management system 40 is to automate the tasks of investigating, manipulating, harvesting and storing small solids that are in large numbers in liquids, illustrated by harvesting protein crystals. The system 40 includes two supporting structures 42 and 44 that each support a pipette tray 43 and 45, respectively. A plurality of pipettes 46 are placed into pipette trays 43 and 45. As illustrated in FIG. 3, tray 43 supports six pipettes 46 and tray 45 supports six pipettes 46. The pipettes are in tip-to-tip relationship when mounted in the trays 43 and 45. The tip of a pipette on tray 43 and the tip of a corresponding pipette on tray 45 may be brought into physical contact by gap drives 48, which defines the fluid/solid working point 50. These working points 50 between pipettes also defines a plane in which the robotic arm 20 is mounted.

The corresponding pipettes 46' and 46" are movable toward and away (x axis) from each other by gap drives 48 in a linear manner that move the trays 43 and 45. The trays 43 and 45 are also movable toward the front or back (y axis) of the assembly 12 by pipette change out drives 52. The movement of the trays 43 and 45 by the change out drives 52 enables the desired pipettes to be aligned with the pipette plunger actuators 54' and 54". The movement of the trays 43 and 45 enables any pipette on one tray to be aligned with any pipette on the other tray, illustrated by pipettes 54' and 54", and having the pipette plunger actuators aligned with the plungers of those selected pipettes.

Referring back to FIG. 1, a microscope camera 56 provides a polarized and magnified view of the candidate crystal to be harvested. A backlight/polarizer 58 is positioned below a desired corresponding pair of pipette ends at the fluid/solid working point 50.

Figure 4:
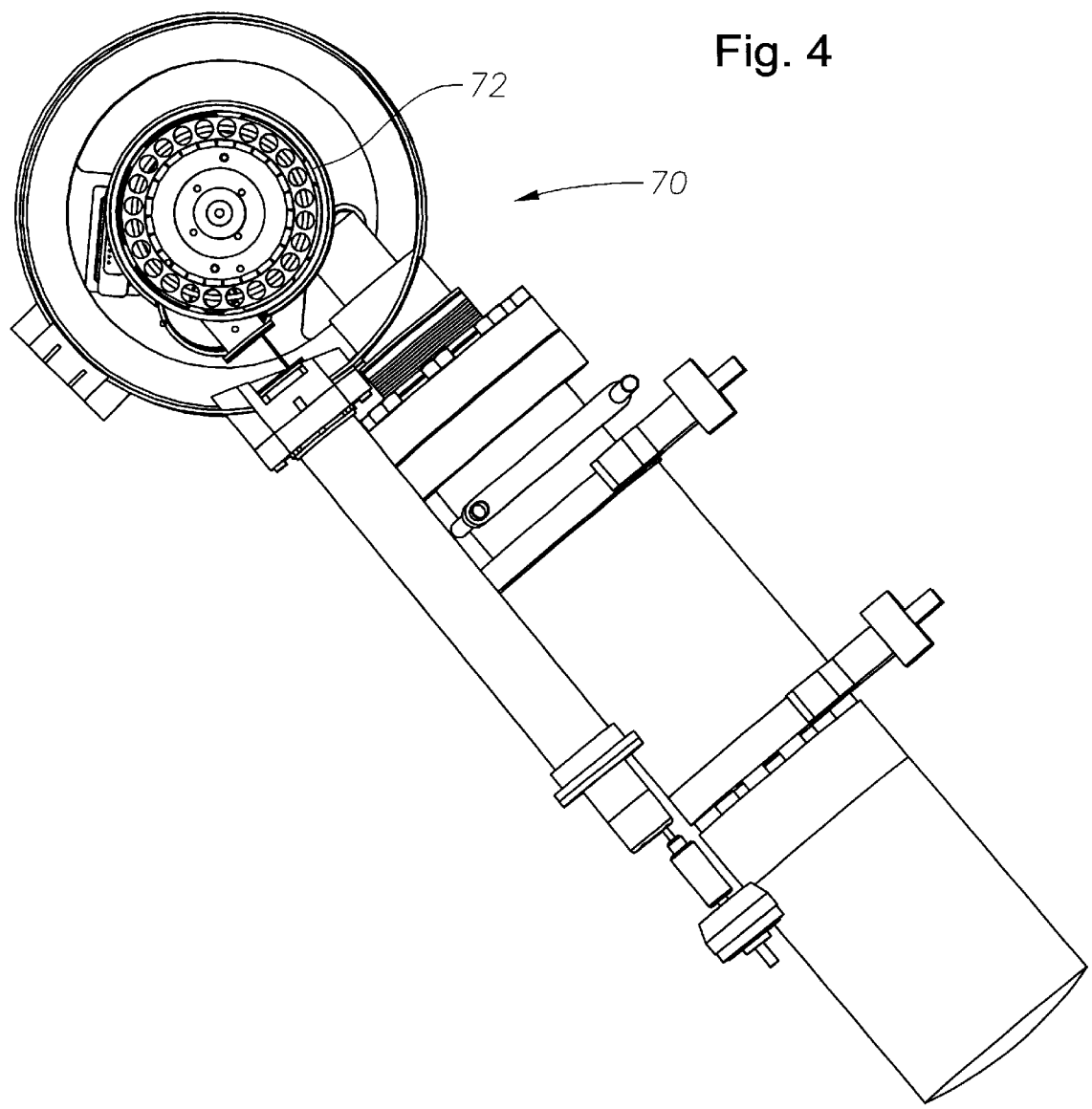
FIG. 4 is an isometric view of a flash freezer and storage carousel.

The protein crystal harvesting system also includes a flash freezer 70. A flash freezer unit is installed in the position shown in FIG. 1. The flash freezer 70 shown in FIG. 4 functions as a freezer and storage unit. The design of the flash freezer 70 is as a storage carousel 72. The details of storage carousel 72 will be described hereinafter.

The operation of the system 10 is illustrated by giving a brief description of the steps necessary to harvesting protein crystals. The protein has already been produced, for example as an expressed protein. The protein is in a mother liquor and the number of molecules of the protein are large. The production and duplication operations to produce a high density of the desired protein are known and are not part of the present invention. Neither is the crystalization procedure of the protein a part of the present invention.

The harvesting system of the present invention, as illustrated by harvesting protein crystals, begins with crystalized protein in high densities, meaning a large numbers of crystals. These crystals in the mother liquor are placed in a cell of a block 34 of a cartridge 32. The system 10 is environmentally sealed and allows the operations to be carried out without contamination. The preparation of the fluid/solid management system may include filling at least one pair of corresponding pipettes with mother liquid at a desired viscosity. The object of the fluid management system is to form a liquid bridge between the tips of the corresponding pipettes. The corresponding pipettes are moved to a position where the tips essentially touch and each pipette has a drop of fluid at its end. The pipettes are then moved apart to form the liquid bridge. The gap may range from about 0.05 to 0.5 inches or 0.127 to 1.27 centimeters. The specific gap is only to provide a working area for the crystal preparation and harvesting operation. Other corresponding pipettes may be filled with differing molar concentrations of a desired cryo-protectant. The specific materials and concentrations are known for a particular protein.

Figure 5:
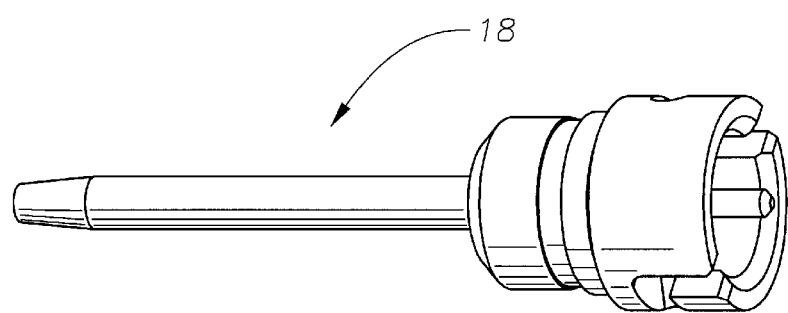
FIG. 5 is an isometric view of a pipette tool that is used to extract protein crystals and mother liquor from high density protein crystal growth cells.
Figures 6A, 6B:
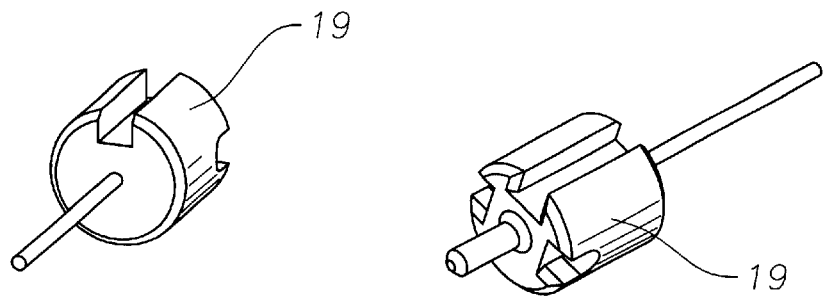
FIG. 6 is an isometric view of each (a) and (b) end of a hairloop tool that is used to mount a crystal that is destined to be flash frozen.

The system 10 of the present invention is closed and the chamber 14 cooled or warmed as desired by circulating water in the assembly 12 to begin the preparation and harvesting operation. The robotic arm 20 is activated and the end effector 24 will engage and remove a cell containing the protein crystals from the cartridge 32, remove the cap on the cell. The robotic arm 20 with end effector 24 attaches to one of the pipette tools 18, shown in FIG. 5. The desired pipette tool 18 extracts a desired amount of mother liquor and crystals from the cell. The base of the pipette tool permits attachment to the end effector 24 via a j-lock. The sensors in the end effector 24 allow for the precise measurement of the fluid extracted from the cell and inserted into the bridge of mother liquor between two corresponding pipettes on the management system 40. The liquid is moved slowly back and forth between tips of the pipettes to isolate crystals in the bridge. The backlight/polarizer 58 is positioned below the corresponding pair of pipette ends at the fluid/solid working point 50 and the microscope camera 56 is activated to provide a polarized and magnified view of crystals in the bridge. A candidate crystal is identified to be harvested. The view will assure that the desired crystal is positioned in the bridge to be prepared and harvested. The robotic arm is actuated to change the pipette tool 18 for one of the hairloop tools 19. The hairloop of the hairloop tool 19 is used to harvest the desired crystal from the bridge.

Once a crystal is harvested from the mother liquor, the crystal is flash frozen for storage or placed into a capillary storage container. If the crystal is be flash frozen, the crystal is prepared with a cryo-protectant to protect the crystal. A known protectant for the crystal is known; however, the crystal may not be placed into the protectant but must be treated in steps. The dilution or molar concentration of the cryo-protectant may be stepwise raised to maintain the integrity of the crystal. This process is carried out in two or more pairs of the corresponding pipettes. The hairloop tool 19 is used to transfer the crystal to the liquid bridges between corresponding pipettes. After the final preparation, the crystal is introduced to the flash freezer and storage carousel 72.

The flash freezer 70 is designed to snap freeze the crystal and also to store the frozen crystal. The carousel 72 is designed to hold a plurality of frozen crystals, twenty-four openings shown in FIG. 4. The flash freezer uses liquid nitrogen as the preferred cryogen. The temperature within the opening and inside the storage area is maintained at −183° C. through direct and indirect contact with the mechanical cryocooler (not shown). The introduction of the hairloop tool 19 with a crystal on the hairloop will snap freeze the crystal. Once frozen, the hairloop tool 19 is fully inserted into the carousel 72 where it is detached from the end effector 24. The frozen crystal is then stored in the carousel 72 maintained at −183° C. until needed for the next operation.

Figure 7:
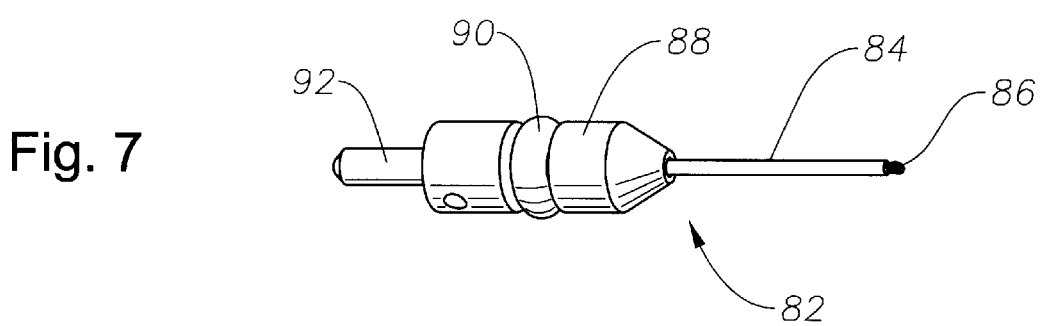
FIG. 7 is an isometric view of a solid mounted on another embodiment of a hairloop tool.
Figure 8:
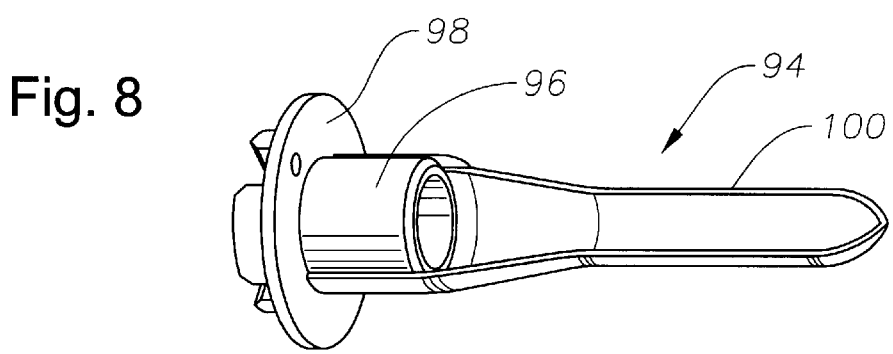
FIG. 8 is an isometric view of a capillary for storing a mounted solid.
Figure 9:
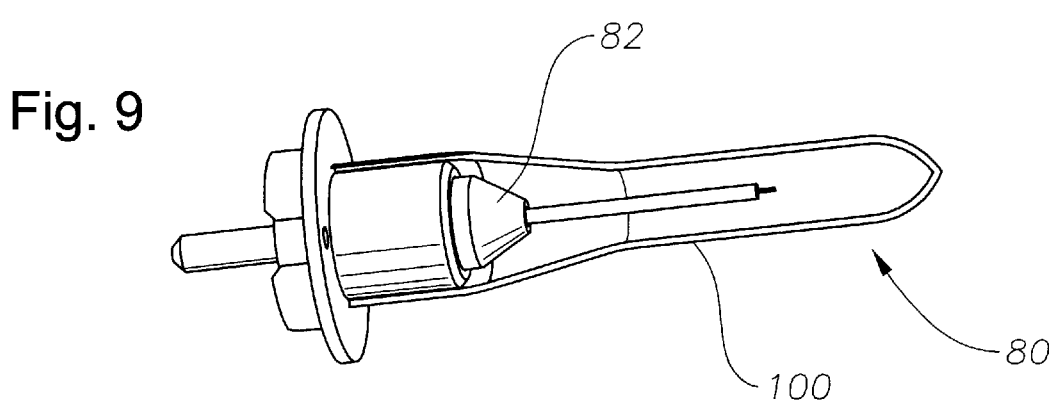
FIG. 9 is an isometric view of a solid, especially a small solid, mounted on the hairloop tool of FIG. 7 sealed in the capillary of FIG. 8.

Alternatively, a harvested crystal will be removed from a liquid bridge with a hairloop tool as shown in FIG. 7. This tool 82 is part of an alternative storing device 80. The tool has a thin cylinder member 84 with a hairloop 86 on the end. A large diameter portion 88 has an o-ring 90 in a groove in portion 88. A handle 92 is at the other end of the tool 82. The tool 82 fits into a capillary 94. The capillary 94 is comprised of an open tubular base 96 with a large ring 98 and a capillary tube 100. The capillary tube 100 has an enlarged end that snugly fits over the base 96 and against the enlarged ring 98.

What is claimed is:

1. A system for the harvesting of solids from liquids comprising:

a chamber;

a fluid/solid management system having at least two pipettes in said chamber, each pipette aligned tip-to-tip and separated by a working point; and a robotic arm for harvesting said solids at said working point between the tips of said pipettes.

2. A system according to claim 1 wherein said solids comprise a protein crystal.

3. A system for the harvesting of protein crystals according to claim 2 which further includes:

a flash freezing system in said chamber for freezing said harvested protein crystals.

4. A system for the harvesting of solids according to claim 1 wherein said fluid/solid management system includes:

two supporting structures for a plurality of said pipettes, at least one said pipette on one structure and at least one said pipette on said second structure, each pipette having a tip end and a plunger end and oppositely directed such that the tips are directed toward each other;

two pipette plunger actuators, one positioned at the plunger end of the pipette on one structure and the other positioned at the plunger end of the pipette of said second structure;

means for adjusting the distance between said pipette on one supporting structure and the pipette on said second supporting structure; and means for aligning said pipette actuators at the plunger ends of two pipettes that are aligned with each other on the respective supporting structures.

5. A system for the harvesting of solids according to claim 1 which further includes:

a tool box on a wall of said chamber.

6. A process for the robotic harvesting of a solid with a robotic arm comprising:

isolating a solid in a liquid bridge between two pipettes aligned tip-to-tip; and harvesting said solid from said liquid bridge with a harvesting device connected to said robotic arm.

7. A process for the robotic harvesting of solids according to claim 6 wherein said solid is a protein crystal.

8. A process according to claim 7 which further includes:

flash freezing said crystal.

9. A fluid/solid management system which comprises:

two supporting structures for a plurality of pipettes, at least one pipette on one structure and at least one pipette on said second structure, each pipette having a tip end and a plunger end and aligned tip-to-tip;

two pipette plunger actuators, one positioned at the plunger end of the pipette on one structure and the other positioned at the plunger end of the pipette of said second structure;

means for adjusting the distance between said pipette on one supporting structure and said pipette on said second supporting structure; and means for aligning said pipette actuators at the plunger end of two pipettes that are aligned with each other on the respective supporting structures.

10. A fluid/solid management system according to claim 9 which further includes:

a robotic arm located on the axis of a working point between the ends of said pipettes.

11. A system for the harvesting of solids from liquids comprising:

a chamber;

a fluid/solid management system having at least two pipettes in said chamber, said pipettes aligned tip-to-tip and separated from each other to form a liquid bridge in which the solid is harvested and defining a working point in said chamber; said management system including:

two supporting structures for a plurality of pipettes, at least one said pipette on one structure and at least one said pipette on said second structure;

two pipette plunger actuators, one positioned at the plunger end of the pipette on one structure and the other positioned at the plunger end of the pipette of said second structure; and a robotic arm for harvesting said solids at said working point between the tips of said pipettes.

12. A system for the harvesting of solids from liquids having a fluid/solid management system according to claim 11 which further includes:

means for adjusting the distance between said pipette on one supporting structure and the pipette on said second supporting structure.

* * * * *